(12) United States Patent
Higgins

(10) Patent No.: US 8,626,317 B2
(45) Date of Patent: Jan. 7, 2014

(54) BITE BLOCK

(75) Inventor: James Higgins, Phoenix, AZ (US)

(73) Assignee: ProNerve, LLC, Broomfield, CO (US)

( * ) Notice: Subject to any disclaimer, the term of this patent is extended or adjusted under 35 U.S.C. 154(b) by 338 days.

(21) Appl. No.: 12/951,975

(22) Filed: Nov. 22, 2010

(65) Prior Publication Data

US 2012/0130216 A1 May 24, 2012

(51) Int. Cl.
 *A61N 1/00* (2006.01)
 *A61C 3/00* (2006.01)
 *A61B 5/00* (2006.01)

(52) U.S. Cl.
 USPC .............................. 607/134; 433/32; 600/582

(58) Field of Classification Search
 USPC ........... 433/32, 38–42, 71–76, 80, 82, 93–94, 433/136–140; 600/372–373, 383, 393, 590; 607/115–116
 See application file for complete search history.

(56) References Cited

U.S. PATENT DOCUMENTS

| 3,483,619 A | 12/1969 | Smith |
| 3,924,333 A | 12/1975 | Erickson |
| 4,167,814 A | 9/1979 | Schubert |
| 4,975,057 A | 12/1990 | Dyfvermark |
| 5,009,595 A | 4/1991 | Osborn |
| 5,190,053 A * | 3/1993 | Meer .............................. 607/134 |
| 5,211,556 A * | 5/1993 | Kobayashi et al. ............. 433/72 |
| 5,212,476 A * | 5/1993 | Maloney ...................... 340/4.11 |
| D348,932 S | 7/1994 | Jackson |
| 5,769,635 A | 6/1998 | Eldreth |
| D397,442 S | 8/1998 | Kittelsen |
| 6,212,435 B1 * | 4/2001 | Lattner et al. ................. 607/134 |
| 6,974,321 B2 | 12/2005 | Hirsch et al. |
| D536,441 S | 2/2007 | Garren et al. |
| D605,285 S | 12/2009 | Garren et al. |
| 2007/0218422 A1 | 9/2007 | Ehrenfeld |
| 2008/0053434 A1 | 3/2008 | Wightman et al. |
| 2008/0090200 A1 | 4/2008 | Hirsch et al. |
| 2008/0234604 A1 * | 9/2008 | Burgmans ..................... 600/582 |
| 2008/0318183 A1 | 12/2008 | Suzman |
| 2012/0315596 A1 * | 12/2012 | Gan et al. ........................ 433/32 |

* cited by examiner

*Primary Examiner* — Linda Dvorak
*Assistant Examiner* — Brian M Antiskay
(74) *Attorney, Agent, or Firm* — Perkins Coie LLP

(57) ABSTRACT

A bite block for use during intraoperative monitoring of nerves is provided. The bite block is formed of a resilient material to inhibit injury to one or more teeth or the tongue of the patient. The bite block includes at least one access port angled with the respect to a plane and sized to slidingly receive an electrode. The electrode may be advanced through the access port and into the tongue of the patient.

11 Claims, 8 Drawing Sheets

BITE BLOCK

CLAIM OF PRIORITY UNDER 35 U.S.C. §119

None.

CLAIM OF PRIORITY UNDER 35 U.S.C. §120

None.

REFERENCE TO CO-PENDING APPLICATIONS FOR PATENT

None.

BACKGROUND

1. Field

The technology of the present application relates generally to devices to inhibit a surgical patient's bite during surgical operations and, more particularly, to a resilient bite block for placement in a mouth with at least one electrode access bore to facilitate placing an electrode in the tongue of a patient for intraoperative monitoring (IOM) during the surgical operations.

2. Background

The tongue is a muscle that has its movement stimulated by nerves such as, for example, the XIIth Cranial Nerve hypoglossal nerve. The movement of the tongue is useful in swallowing and making sounds associated with speech among other things. Thus, damage to the nerves associated with the control of the tongue is potentially severe as it may inhibit a person's ability to eat and speak. Moreover, bite block inhibits the ability of the person to bite the tongue and inhibits potential tooth and/or jaw damage associated with severe clamping of the jaws after transcranial electrical stimulation for motor evoked potentials. To monitor for potential damage to the nerves associated with the tongue's muscle control, a bipolar or monopolar recording electrode is placed about the tongue. The tongue is activated when the XIIth CN is mechanically or electrically stimulated during the surgical intervention. The recording electrodes in the tongue are used to record the electromyelographic response of the activated muscles in the tongue.

As can be appreciated, the electrodes are placed by a trained technician locating the electrodes on the tongue. To do this, the technician opens the mouth of a patient and places an electrode. For example, the technician may advance a needle electrode into the tongue until the electrode is proximate the muscle the electrode will record. The mouth is often propped open using an object in the mouth generally known as a bite block. The bite block is positioned between the teeth of a patient to inhibit the mouth from closing. Wires from the electrode are connected to an amplifier as is common in the art.

The bite block often if formed of a hard plastic material. The hard plastic material may in some instances cause injury to the teeth of the patient, such as, for example, a chipped or cracked tooth. Also, the bite block occupies a portion of the patient's mouth and can make placement of the recording electrode difficult. Moreover, the bite block takes up a significant volume in the patient's mouth that may hinder placement of the needle electrode in certain cases.

Thus, against this background, it would be desirous to provide an improved bite block that would be less likely to injury the teeth of the patient as well as facilitate rather than hinder placement of the recording electrode.

SUMMARY

Embodiments disclosed herein address the above stated needs by providing a bite block adapted for use during intraoperative monitoring of nerves associated with the mouth or tongue of a patient. The bite block includes a resilient left portion having an inside face and an outside face separated by a width, a front face and a back face separated by a depth, and a top face and a bottom face separated by a height as well as a resilient right portion having an inside face and an outside face separated by a width, a front face and a back face separated by a depth, and a top face and a bottom face separated by a height. The resilient left and right portions are connected by a flexible bridge adapted to extend across at least a portion of a mouth of a patient. An access port resides in at least one of the resilient left portion or the resilient right portion, the access port having a first opening and a second opening residing in the inside face formed opposite the first opening and forming a through bore in the at least one of the resilient left portion or the resilient right portion from the first opening to the second opening, the first opening being arranged a first distance from the top face and the second opening being arranged a second distance from the top face where the second distance is greater than the first distance.

Embodiments disclosed herein address the above stated needs by providing a method for using a bite block adapted for use during intraoperative monitoring of nerves associated with the mouth or tongue of a patient. The procedure includes placing the bite block in the mouth of the patient. In some cases, the placement includes arranging a tab associated with the bridge of the bite block to cause the tongue of the patient to bulge. An electrode is then placed through a bore in the bite block until the electrode is properly placed for intraoperative monitoring of the XIIth Cranial Nerve hypoglossal nerve.

DETAILED DESCRIPTION

The technology of the present application will now be described with reference to the attached FIGS. 1-7. While the technology of the present application is described with reference to a bite block useful for measuring the CN XII—

Hypoglossal Nerve—during intraoperative monitoring (IOM) associated with certain surgical procedures, one of ordinary skill in the art will recognize on reading the disclosure that the bite block may be useful for facilitating separation of the mouth in procedures where teeth may be injured, chipped, cracked or the like. Additionally, while the technology of the present application is described with regards to advancing a needle electrode or the like, other electrodes and other instruments that require specific placement in the mouth may benefit from the technology of the present application. Moreover, the technology of the present application will be described with reference to particular exemplary embodiments. The word "exemplary" is used herein to mean "serving as an example, instance, or illustration." Any embodiment described herein as "exemplary" is not necessarily to be construed as preferred or advantageous over other embodiments unless specifically indicated as such. Thus, the examples provided should be considered illustrative of the technology of the present application and not limiting.

Figure 1:
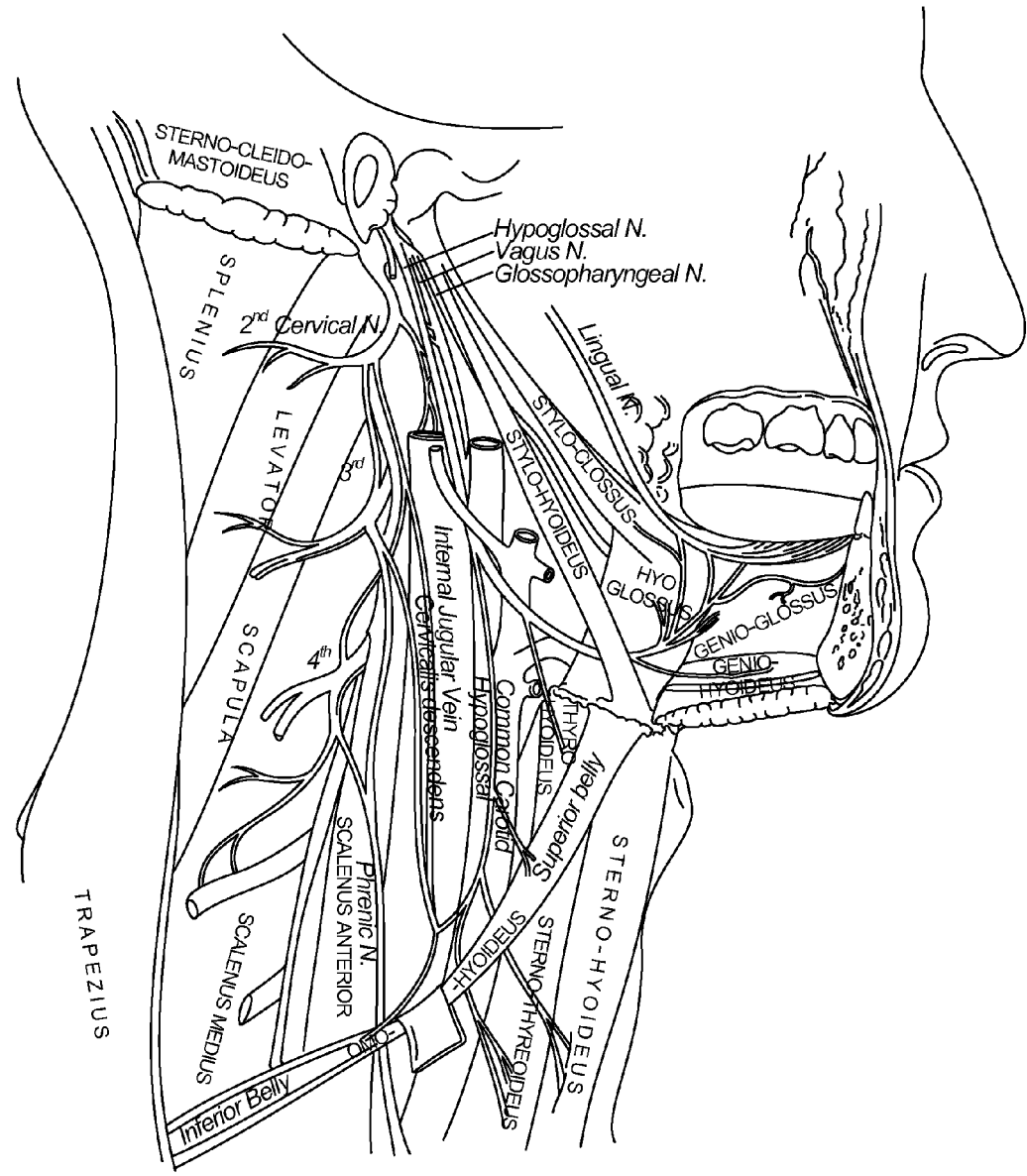
FIG. 1 is a view of anatomy associated with the mouth and tongue of a patient.

Referring first to FIG. 1, anatomy associated with the tongue is provided. In particular, the hypoglossal nerve is the twelfth cranial nerve [CN XII] leading to the tongue. It supplies motor signals to a majority of the muscles of the tongue. Thus, the hypoglossal nerve facilitates functions such as swallowing, chewing, speech, and the like.

As explained above, IOM of the hypoglossal nerve may be used in certain surgeries to alert surgeons to potential issues or damage to the nerve, which may inhibit muscle function of the tongue. Some surgeries that may benefit from monitoring of the hypoglossal nerve include, for example, surgery relating to brainstem tumors, brainstem cavernous malformations, brainstem aneurysms and other surgical procedures in which the hypoglossal nerve may be inadvertently damaged such as common carotid artery or internal jugular vein lesions where the hypoglossal nerve may be at risk to name but a few.

Figure 2:
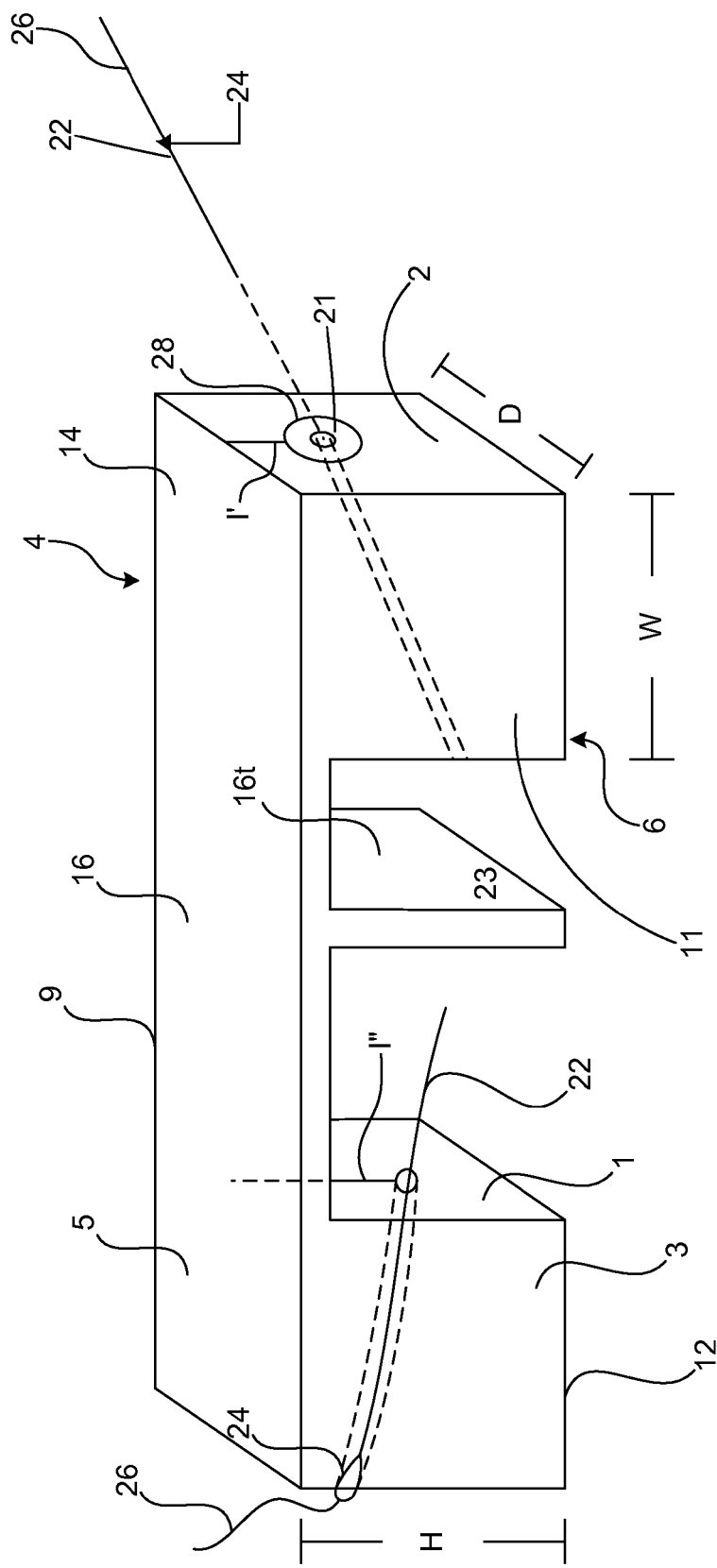
FIG. 2 is a perspective view of a bite block consistent with the technology of the present application.

Referring now to FIG. 2, a bite block 10 consistent with the technology of the present application is shown. The bite block 10 is shown with left and right portions 12, 14 generally rectangular in shape, although the shape is optional. The left and right portions 12, 14 have a width W, a depth D, and a height H as shown. Although shown as symmetrical, the left and right portions do not need to be shaped the same.

The height H is generally chosen as appropriate to keep the mouth of the patient open. The width W is typically the approximate width of a tooth, such as, for example, a molar, an incisor, or the like depending on placement. Typically the width W would be slightly larger than a tooth to facilitate placement. The depth D is typically approximately the depth of a single tooth, but may be longer than one tooth and may bridge several teeth. Width W generally separates an inside face 1 and an outside face 2. Depth D generally separates a front face 3 and a back face 4. Height H generally separates a top face 5 and a bottom face 6. As mentioned above, while generally described as rectangular, the left and right portions may be any shape including circular, elliptical, polygonal, or random shapes such that the faces may be a relatively flat sidewall as shown, curved portions of the device, or potentially multifaceted.

The left and right portions 12, 14 may be separate pieces that function in cooperation with each other or connected by bridge 16 as shown. It is believed a bridge 16 would facilitate placement of the bite block 10 by the anesthesiologist, surgeon, nurse, or other O.R. personnel. The bridge 16 may be integrated to each portion 12, 14 such that the bite block 10 functions as a single unit. The bridge 16 is shown as being flat across from the left and right portions 12, 14. Optionally, bridge 16 may be shaped to conform to the roof of the patient's mouth. Alternatively, bridge 16 may be shaped to hold the tongue in a desired position. In certain embodiments, a tab 16t may be associated with the bridge 16 to hold the tongue down so that the sides of the tongue bulge, which makes the tongue taut. The bulging and tautness of the tongue is beneficial for puncturing the tongue with the electrode. Tab 16t (only shown in FIG. 2 for convenience) may be located proximate one or the other of the left and right portions to facilitate bulging of the tongue. Moreover, the tab 16t may be modular and removable such that the tab 16t may be removed after the placement of an electrode. Also, while only one tab 16t is shown, the tabs may be on one or both sides of the bridge 16. In still other embodiments, the tab 16t may extend off of one or both of the resilient left and right portions. The bridge 16 may be a flexible material such as a plastic or composite strap, thong, or the like.

As shown in FIG. 2, both the left and right portions 12, 14 have an access bore 20. Access bores 20 are sized to fit a needle electrode 22 snuggly, but slidingly. Needle electrode 22 is slidingly advanced into and through access bore 20 until the needle electrode 22 is properly inserted into the tongue of the patient. To facilitate placement, the needle electrode 22 may incorporate a stop 24 that abuts left or right portion 12, 14 to stop advancement of the needle electrode 22 when it is properly inserted. As shown, needle electrode 22 has a flared stop 24 that forms a friction fit with access bore 20 to positively stop needle electrode 22 and hold the needle electrode 22 in place until it is removed by the surgeon. The leads 26 extend from stop 24. Access bore 20 may be substantially cylindrical in shape as shown. Alternatively, access bore 20 may be conical to cooperatively engage stop 24. As will be explained further below, access bore 20 is a through bore extending from a first opening 21 on outside face 2 that is a first distance I' from the top face 5 to a second opening 23 on inside face 1 that is a second distance I" from the top face 5. The second distance I" is greater than first distance I' such that the access bore 20 forms an angle with a plane defined by the tongue as explained further below.

Figure 3:
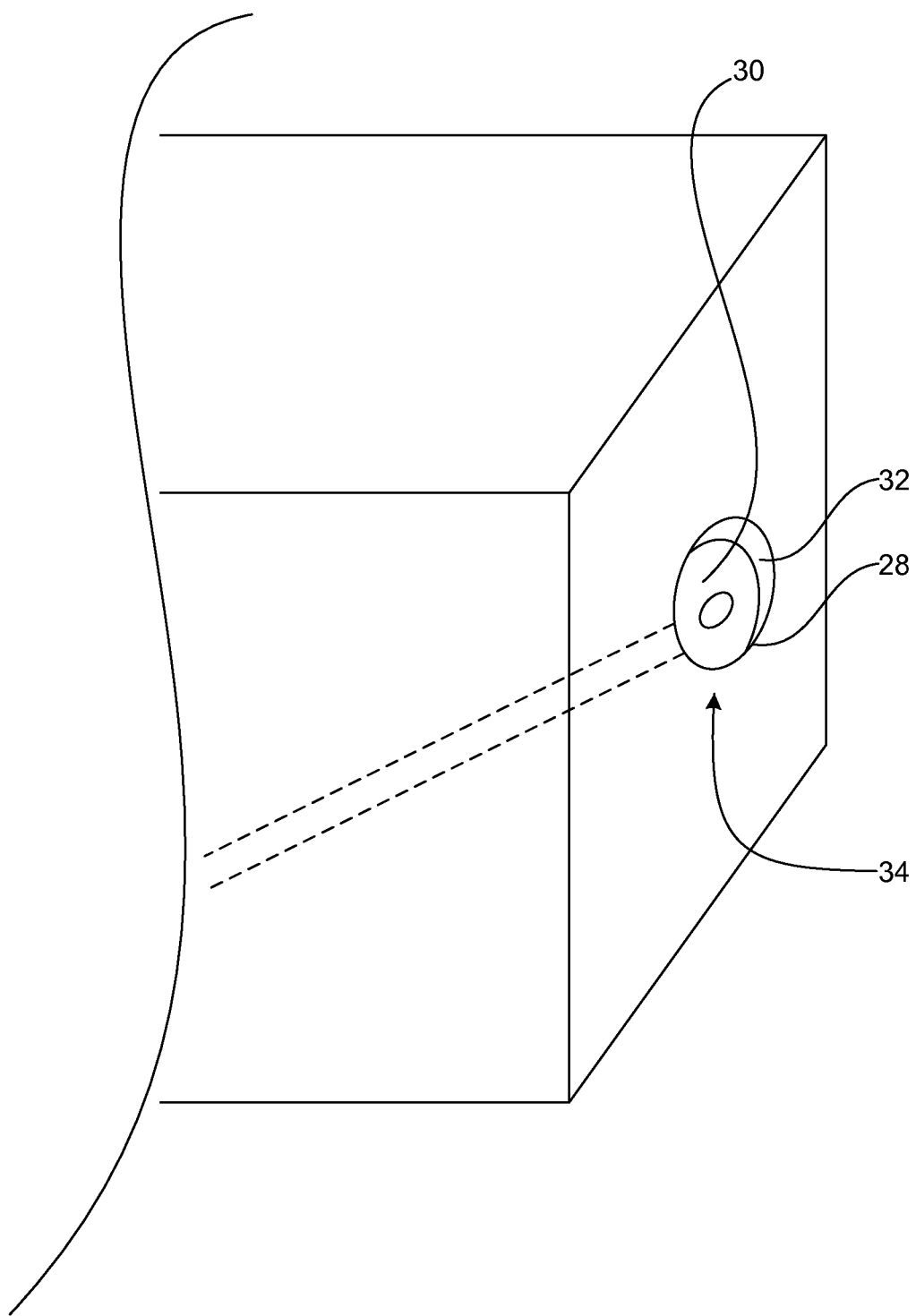
FIG. 3 is a perspective view of a portion of the bite block of FIG. 2 consistent with the technology of the present application.

In still other embodiments, access bore 20 may be located in a countersunk bore 28 as shown in FIG. 3. Countersunk bore 28 has a base or shoulder 30 and sidewalls 32 defining a recess 34. Stop 24 may be sized and shaped to fit within recess 34.

The reason for including the CV XII nerve monitor holes is for procedures in which nerve/muscle monitoring is desirous, such as, for example, when there is a low brainstem tumor or other lesion in which that cranial nerve is at risk. Because transcranial electric motor evoked potentials are needed for these types of procedures, a bite block is typically used and often necessary to inhibit tooth and jaw damage due to the clenching described above. Providing a bite block that facilitates electrode placement and electrode securing is one of several advantages of the present technology.

Bite block 10 may be formed of a variety of materials including, for example, metals, metal alloys, plastics, composites, polymers, gels or the like. Preferably bite block 10 would be formed of a resilient material, such as, for example, a silicone gel, an ethylene-vinyl acetate (EVA), or the like. Forming the bite block 10 out of a resilient material would inhibit damage to one or more teeth. In particular, the mouth may constrict, contract, or close abruptly during surgery, which is one of the reasons bite blocks are used. Providing the bite block 10 out of an inelastic or rigid material, such as a metal, may cause injury to one or more teeth as the rigid material may chip, crack, or break the tooth. The bite block 10 should be sufficiently capable of holding a shape, however, such that constriction, contraction, or closing of the mouth does not move the electrode 22 or cause the electrode 22 to be removed or moved from it desired location. In some cases, bite block 10 may have an outer skin or membrane 9 forming the desired shape of bite block 10 such that a soft filler material 11 may be used in the volume defined by the skin 9. However, it other cases, bite block 10 may be molded from a plastic, composite or gel.

Figure 4A:
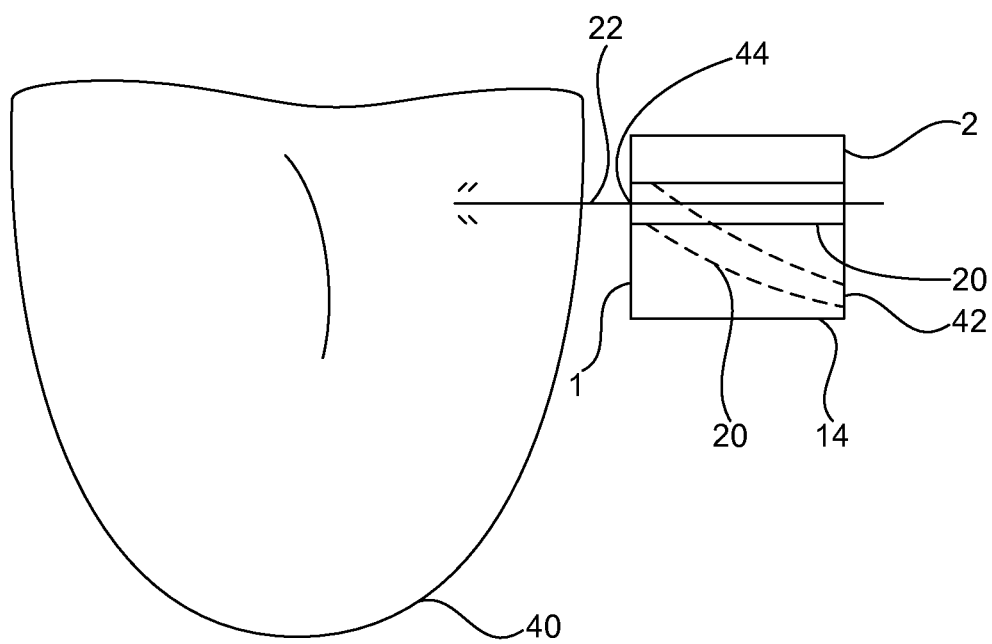
FIG. 4A is a plan view of the bite block of FIG. 2 with a needle electrode extending into the tongue of a patient consistent with the technology of the present application.
Figure 4B:
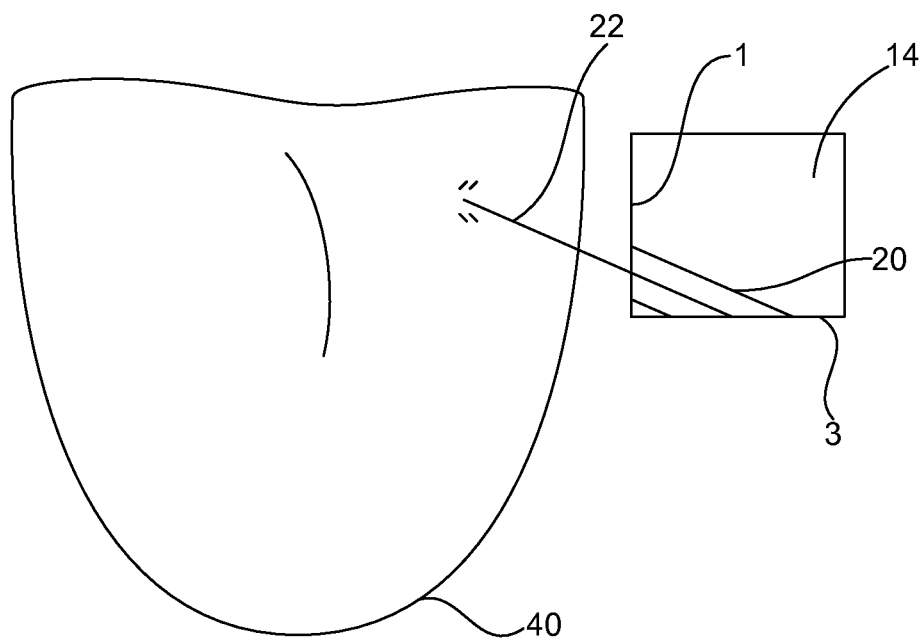
FIG. 4B is a plan view of the bite block of FIG. 2 with a needle electrode extending into the tongue of a patient consistent with the technology of the present application.

Referring now to FIGS. 4A and 4B, a top plan view of the electrode 22 extending through the portion 14 of the bite block 10 into a tongue 40 of a patient is provided. As shown, electrode 22 extend through access bore 20 extending between the outside face 2 and the inside face 1 of the portion 14. It may be difficult in certain patient anatomy to arrange the bite block 10 to allow the electrode 22 to extend laterally as shown. Instead of traveling straight across portion 14, access bore may have be located in a first location 42 in the outside face 2 and a second location 44 in the inside face such that the first location 42 is anterior or forward of the second location as shown by the access bore 20 in phantom in FIG. 4A. Alternatively, as shown in FIG. 4B, the access bore 20 may be arranged between the front face 3 and the inside face 1.

Figure 5:
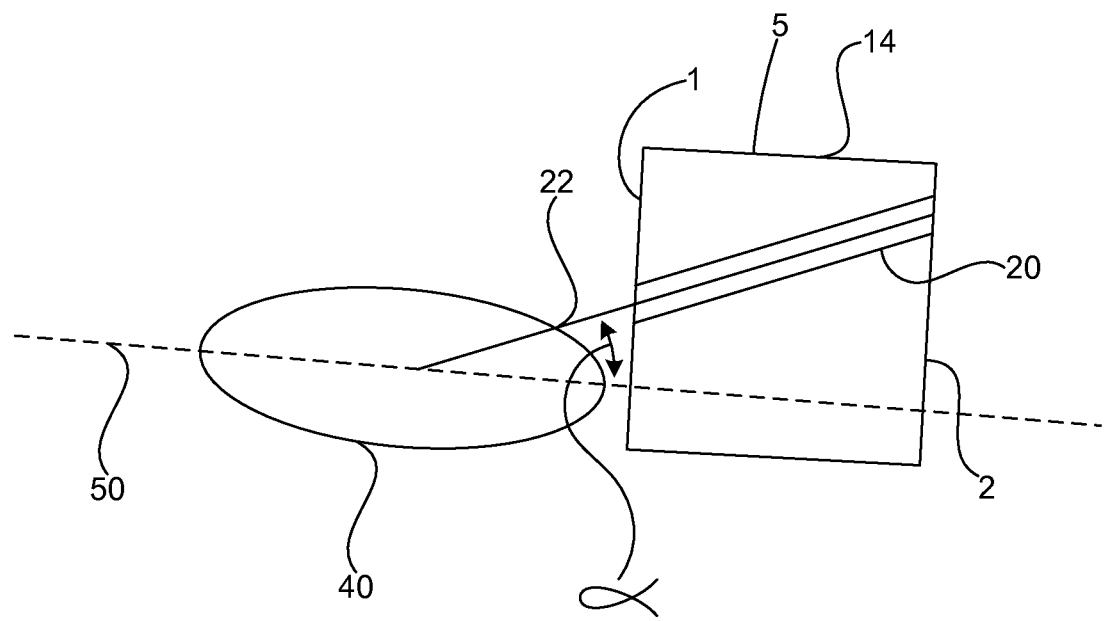
FIG. 5 is a front elevation view of the bite block of FIG. 2 with a needle electrode extending into the tongue of a patient consistent with the technology of the present application.

Referring now to FIG. 5, a side elevation view of electrode 22 extending through the portion 14 is provided. Access bore 20 is shown as extending from the outside face 2 to the inside face 1, but alternative arrangements are possible as explained above. The access bore 20 is arranged in portion 14 such that the bore 20 at the outside face 2 is closer to the top face 5 than the bore 20 at the inside face 1. This provides for the electrode 22 to exit access bore 20 and approach the tongue at an angle $\alpha$ with respect to a plane 50 shown in the FIG. 5. The angle $\alpha$ facilitates insertion of electrode 22 to the appropriate position in the tongue 40.

While FIGS. 4A, 4B, and 5 expressly show portion 14, it should be appreciated that portion 12 may have similar features. While in some situations, a needle electrode 22 will be inserted through one of the left or right portions 12, 14, in some cases a needle electrode 22 will be inserted through both of the left and right portions 12, 14.

Figure 6:
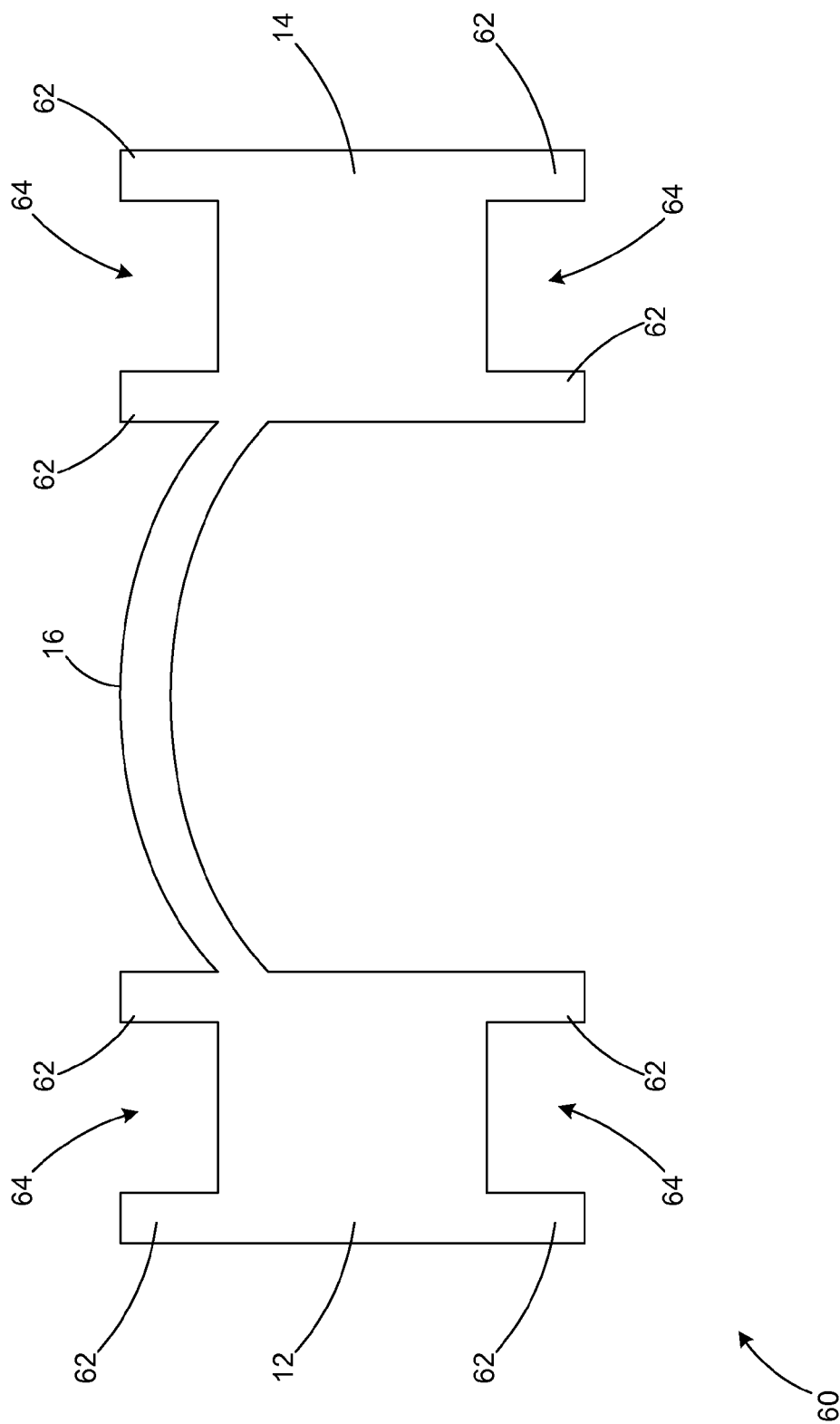
FIG. 6 is an elevation view of a bite block consistent with the technology of the present application.
Figure 7:
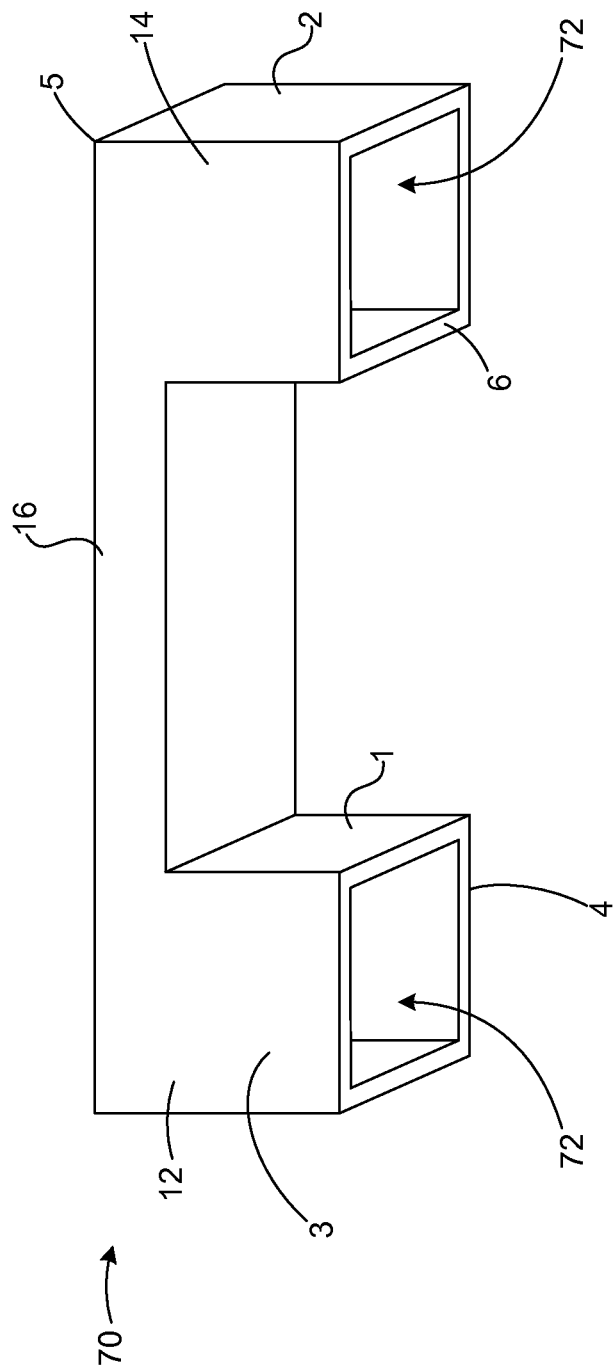
FIG. 7 is a perspective view of a bite block consistent with the technology of the present application.

Referring to FIGS. 6 and 7, the bite blocks 60 and 70 are provided. Similar to bite block 10, the bite block 60 has the left and right portions 12, 14 connected by a bridge 16, which is shown as being adapted to cooperatively engage the roof of a patient's mount in FIG. 6. As shown, each of the left and right portions 12, 14 as inside and outside extensions or protrusions 62 forming a channel or groove 64. The grooves 64 would be sized such that one or more teeth would fit within groove 64. As shown in FIG. 7, the bite block 70 may be provided with a cavity 72 to substantially encompass the crown of a tooth. Grooves 64 and cavities 72 are provided to more securely retain the bite blocks in place.

In use, the bite block 10, 60, or 70 would facilitate insertion of an electrode into a tongue of a patient for IOM. After opening the mouth and angling the head to the desired surgical position, the bite block would be placed by the anesthesiologist, surgeon, nurse, or other O.R. personnel. Once placed, the anesthesiologist, surgeon, nurse, or other O.R. personnel would align an electrode with the access port. The electrode would be slidingly advanced through the access port until it contacts and pierces the tongue of the patient. The electrode would be advanced into the tongue until it is properly positioned to record electromyelographic responses from the CN XII nerve or the like. Notice that the electrodes may be used on one or both sides of the tongue of the patient.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method for positioning an electrode in a mouth of a patient for intraoperative monitoring of at least one nerve associated with a tongue, the method comprising the step of:
    providing a bite block having a left and right portion flexibly connected by a bridge;
    positioning a head of the patient and opening the mouth of the patient;
    placing the bite block in the mouth of the patient to maintain the mouth in an open position;
    aligning an electrode with an access port in at least one of the left and right portion of the bite block;
    advancing the electrode through the access port;
    piercing the tongue of the patient with the electrode during the advancement of the electrode through the access port; and
    stopping the advancement of the electrode when the electrode is properly positioned.

2. The method of claim 1 wherein the step of stopping the advancement of the electrode includes holding the electrode in place during a surgical procedure.

3. The method of claim 2 further comprising the step of removing the electrode when intraoperative monitoring is no longer required.

4. The method of claim 1 wherein stopping the advancement of the electrode comprising abutting a stop on the electrode with the access port.

5. A method of monitoring a hypoglossal nerve, XIIth Cranial Nerve, of a patient during a surgical procedure, the method comprising:
    placing a bite block having a left and right resilient portion in a mouth of the patient;
    arranging the bite block such that an access port in at least one of the resilient left portion or the resilient right portion is aligned with the hypoglossal nerve;
    inserting an electrode through the access port into the tongue of the patient wherein the electrode is aligned and placed for intraoperative monitoring of the hypoglossal nerve.

6. The method of claim 1 wherein a step of placing the bite block in the mouth of the patient further comprises the step of holding a tongue of the patient.

7. The method of claim 6 wherein holding the tongue of the patient comprises placing a tab extending from the bridge to the tongue.

8. The method of claim 6 wherein the step of holding the tongue of the patient comprises causing the tongue to bulge.

9. The method of claim 6 further comprising the step of removing the tab subsequent to the step of stopping advancement of the electrode.

10. The method of claim 1 wherein stopping the advancement of the electrode comprising forming a frictional engagement between the electrode and the access port.

11. The method of claim 1 wherein a step of placing the bite block in the mouth of the patient further comprises conforming the bridge to a roof of the mouth.

* * * * *